(12) United States Patent
Gerber et al.

(10) Patent No.: US 8,200,343 B2
(45) Date of Patent: Jun. 12, 2012

(54) IMPLANTABLE MEDICAL ELECTRICAL STIMULATION LEAD FIXATION METHOD AND APPARATUS

(75) Inventors: Martin T. Gerber, Maple Grove, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 85 days.

(21) Appl. No.: 11/380,493

(22) Filed: Apr. 27, 2006

(65) Prior Publication Data
US 2007/0261115 A1 Nov. 8, 2007

(51) Int. Cl.
*A61N 1/00* (2006.01)
*A61B 5/04* (2006.01)

(52) U.S. Cl. ............... 607/126; 607/127; 600/372

(58) Field of Classification Search ............ 607/127, 607/126; 600/372
See application file for complete search history.

(56) References Cited

U.S. PATENT DOCUMENTS

| | | |
|---|---|---|
| 4,414,986 A | 11/1983 | Dickhudt et al. |
| 4,419,819 A | 12/1983 | Dickhudt et al. |
| 4,465,079 A | 8/1984 | Dickhudt |
| 4,519,403 A | 5/1985 | Dickhudt |
| 5,003,992 A | 4/1991 | Holleman et al. |
| 5,090,422 A | 2/1992 | Dahl et al. |
| 5,129,404 A * | 7/1992 | Spehr et al. ............... 607/127 |
| 5,215,105 A | 6/1993 | Kizelshteyn et al. |
| 5,387,233 A | 2/1995 | Alferness et al. |
| 5,456,667 A | 10/1995 | Ham et al. |
| 5,484,445 A | 1/1996 | Knuth |
| 5,531,779 A | 7/1996 | Dahl et al. |
| 5,723,718 A | 3/1998 | Berens |
| 5,865,843 A | 2/1999 | Baudino |
| 5,957,965 A | 9/1999 | Moumane et al. |
| 5,957,966 A | 9/1999 | Schroeppel et al. |
| 6,055,457 A | 4/2000 | Bonner |
| 6,077,298 A | 6/2000 | Tu et al. |
| 6,104,960 A | 8/2000 | Duysens et al. |
| 6,161,029 A | 12/2000 | Spreigl et al. |
| 6,322,559 B1 * | 11/2001 | Daulton et al. ............... 606/41 |
| 6,325,797 B1 | 12/2001 | Stewart et al. |
| 6,388,043 B1 | 5/2002 | Langer et al. |
| 6,580,949 B1 | 6/2003 | Tsuboi et al. |
| 6,704,604 B2 | 3/2004 | Soukup et al. |
| 6,711,443 B2 | 3/2004 | Osypka |

(Continued)

FOREIGN PATENT DOCUMENTS
CA 2527976 A1 7/2006
(Continued)

OTHER PUBLICATIONS

U.S. Appl. No. 11/380,511 Non-Final Office Action dated Oct. 30, 2009.

(Continued)

*Primary Examiner* — Nicole F Lavert

(57) ABSTRACT

The invention includes a implantable medical electrical lead for electrical stimulation of body tissue that includes at least one electrode; a lead body; and at least one modifiable portion, wherein the at least one modifiable portion has a first configuration and a second configuration, wherein the first configuration exists when axial tension is exerted on the at least one modifiable portion, and wherein the second configuration exhibits a greater resistance to movement of the lead within the body tissue than does the first configuration. Kits, and systems and methods of using the lead are also included.

28 Claims, 10 Drawing Sheets

U.S. PATENT DOCUMENTS

| | | | |
|---|---|---|---|
| 6,720,402 | B2 | 4/2004 | Langer et al. |
| 6,909,920 | B2 | 6/2005 | Lokhoff et al. |
| 6,952,613 | B2 | 10/2005 | Swoyer et al. |
| 6,999,819 | B2 | 2/2006 | Swoyer et al. |
| 7,099,718 | B1 | 8/2006 | Thacker et al. |
| 7,107,105 | B2 | 9/2006 | Bjorklund et al. |
| 7,155,293 | B2 | 12/2006 | Westlund et al. |
| 7,272,448 | B1 | 9/2007 | Morgan et al. |
| 2002/0077684 | A1 | 6/2002 | Clemens et al. |
| 2002/0095114 | A1 | 7/2002 | Palasis |
| 2002/0147485 | A1* | 10/2002 | Mamo et al. .................. 607/116 |
| 2003/0050681 | A1* | 3/2003 | Pianca et al. .................. 607/125 |
| 2003/0199961 | A1* | 10/2003 | Bjorklund et al. ............ 607/126 |
| 2004/0176782 | A1 | 9/2004 | Hanse et al. |
| 2004/0215237 | A1* | 10/2004 | Christopherson et al. ........ 607/3 |
| 2004/0230279 | A1 | 11/2004 | Hanse et al. |
| 2004/0230280 | A1 | 11/2004 | Cates et al. |
| 2004/0230281 | A1 | 11/2004 | Heil et al. |
| 2005/0038491 | A1* | 2/2005 | Haack ........................... 607/126 |
| 2005/0060014 | A1* | 3/2005 | Swoyer et al. ................. 607/117 |
| 2005/0096718 | A1 | 5/2005 | Gerber et al. |
| 2005/0288781 | A1 | 12/2005 | Moaddeb et al. |
| 2006/0041089 | A1 | 2/2006 | Mather et al. |
| 2006/0079949 | A1 | 4/2006 | Hine et al. |
| 2006/0247753 | A1 | 11/2006 | Wenger et al. |
| 2007/0073130 | A1 | 3/2007 | Finch et al. |
| 2007/0255365 | A1 | 11/2007 | Gerber |
| 2007/0255366 | A1 | 11/2007 | Gerber |
| 2007/0255383 | A1 | 11/2007 | Gerber |

FOREIGN PATENT DOCUMENTS

| | | |
|---|---|---|
| EP | 861676 | 2/1998 |
| WO | WO-02087690 | 11/2002 |
| WO | WO-2004047914 | 6/2004 |

OTHER PUBLICATIONS

U.S. Appl. No. 11/380,499 Notice of Allowance dated Nov. 3, 2011.
U.S. Appl. No. 11/380,480 Notice of Allowance dated Nov. 17, 2011.
U.S. Appl. No. 11/380,499, Office Action dated Nov. 30, 2009.
Lendlein, et al. Biodegradable, Elastic Shape-Memory Polymers for Potential Biomedical Application, Science, May 2002, 296:5573, p. 1673-1676.
Gerber, Implantable Medical Electrical Stimulation Lead Fixation Method and Apparatus, U.S. Appl. No. 11/380,499, Final Office Action May 28, 2009.
Gerber, Implantable Medical Electrical Stimulation Lead Fixation Method and Apparatus, U.S. Appl. No. 11/380,499, Non-Final Office Action Nov. 26, 2008.
Gerber, Implantable Medical Electrical Stimulation Lead Fixation Method and Apparatus, U.S. Appl. No. 11/380,499, Advisory Action Jul. 17, 2008.
Gerber, Implantable Medical Electrical Stimulation Lead Fixation Method and Apparatus, U.S. Appl. No. 11/380,499, Final Office Action Apr. 29, 2008.
Gerber, Implantable Medical Electrical Stimulation Lead Fixation Method and Apparatus, U.S. Appl. No. 11/380,499, Non-Final Office Action Aug. 28, 2007.
Gerber, Implantable Medical Electrical Stimulation Lead Fixation Method and Apparatus, U.S. Appl. No. 11/380,511, Non-Final Office Action Mar. 5, 2009.
Gerber, Implantable Medical Electrical Stimulation Lead Fixation Method and Apparatus, U.S. Appl. No. 11/380,511, Advisory Action Oct. 30, 2008.
Gerber, Implantable Medical Electrical Stimulation Lead Fixation Method and Apparatus, U.S. Appl. No. 11/380,511, Final Office Action Jul. 28, 2008.
Gerber, Implantable Medical Electrical Stimulation Lead Fixation Method and Apparatus, U.S. Appl. No. 11/380,511, Non-Final Office Action Nov. 15, 2007.
Gerber et al., Implantable Medical Electrical Stimulation Lead Fixation Method and Apparatus, U.S. Appl. No. 11/380,480, Final Office Action May 13, 2009.
Gerber et al., Implantable Medical Electrical Stimulation Lead Fixation Method and Apparatus, U.S. Appl. No. 11/380,480, Non-Final Office Action Nov. 28, 2008.
Gerber et al., Implantable Medical Electrical Stimulation Lead Fixation Method and Apparatus, U.S. Appl. No. 11/380,480, Advisory Action Sep. 9, 2008.
Gerber et al., Implantable Medical Electrical Stimulation Lead Fixation Method and Apparatus, U.S. Appl. No. 11/380,480, Final Office Action Apr. 30, 2008.
Gerber et al., Implantable Medical Electrical Stimulation Lead Fixation Method and Apparatus, U.S. Appl. No. 11/380,480, Non-Final Office Action Aug. 22, 2007.
U.S. Appl. No. 10/380,480 Non-Final Office Action dated Oct. 26, 2009.
U.S. Appl. No. 11/380,480 response filed Jan. 26, 2010.
U.S. Appl. No. 11/380,480 Office Action dated Apr. 30, 2010.
U.S. Appl. No. 11/380,480 response filed Jun. 16, 2010.
U.S. Appl. No. 11/380,499 response filed Feb. 27, 2010.
U.S. Appl. No. 11/380,499 Office Action dated Jun. 11, 2010.
U.S. Appl. No. 11/380,511 response filed Feb. 1, 2010.
U.S. Appl. No. 11/380,511 Office Action dated May 3, 2010.
U.S. Appl. No. 11/380,480 response filed Feb. 18, 2008.
U.S. Appl. No. 11/380,480 response filed Jun. 25, 2008.
U.S. Appl. No. 11/380,480 response filed Mar. 2, 2009.
U.S. Appl. No. 11/380,480 response filed Aug. 13, 2009.
U.S. Appl. No. 11/380,499 response filed Jul. 17, 2008.
U.S. Appl. No. 11/380,499 response filed Jan. 28, 2008.
U.S. Appl. No. 11/380,499 response filed Jun. 28, 2008.
U.S. Appl. No. 11/380,499 response filed Feb. 26, 2009.
U.S. Appl. No. 11/380,499 response filed Aug. 28, 2009.
U.S. Appl. No. 11/380,511 response Apr. 14, 2008.
U.S. Appl. No. 11/380,511 response Sep. 29, 2008.
U.S. Appl. No. 11/380,511 response Dec. 30, 2008.
U.S. Appl. No. 11/380,511 response Jul. 4, 2009.
U.S. Appl. No. 11/380,480 Advisory Action dated Jul. 8, 2010.
U.S. Appl. No. 11/380,480 response filed Aug. 25, 2010.
U.S. Appl. No. 11/380,480 Non-Final Office Action dated Oct. 4, 2010.
U.S. Appl. No. 11/380,480 response filed Dec. 29, 2010.
U.S. Appl. No. 11/380,480 Final Office Action dated Mar. 4, 2011.
U.S. Appl. No. 11/380,499 Office Action dated Nov. 30, 2009.
U.S. Appl. No. 11/380,499 response filed Sep. 10, 2010.
U.S. Appl. No. 11/380,499 Final Office Action Dec. 1, 2010.
U.S. Appl. No. 11/380,499 response filed Mar. 1, 2011.
U.S. Appl. No. 11/380,499 Final Office Action dated Mar. 31, 2011.
U.S. Appl. No. 11/380,511 Final Office Action dated Jul. 28, 2008.
U.S. Appl. No. 11/380,511 Office Action dated Nov. 15, 2007.
U.S. Appl. No. 11/380,511 response filed Aug. 2, 2010.
U.S. Appl. No. 11/380,511 Final Office Action dated Nov. 12, 2010.
U.S. Appl. No. 11/380,511 response filed Feb. 14, 2011.
Lendlein, "Shape Memory Polymers—Biodegradable Sutures", Abstracted from Materials World, Jul. 2002, 10:7, p. 29-30, Website Article: www.azom.com/details.asp?articleID=1542.
Wingfield, "Shape Change Materials", Feb. 2006: 13:08, Website Article: www.loop.ph/twiki/bin/view/Openloop/ShapeChange.
U.S. Appl. No. 11/380,480 Response filed Jun. 6, 2011.
U.S. Appl. No. 11/380,480 Non-Final Office Action mailed Jun. 23, 2011.
U.S. Appl. No. 11/380,499 Response filed Jun. 30, 2011.
U.S. Appl. No. 11/380,480 Response filed Sep. 23, 2011.

* cited by examiner

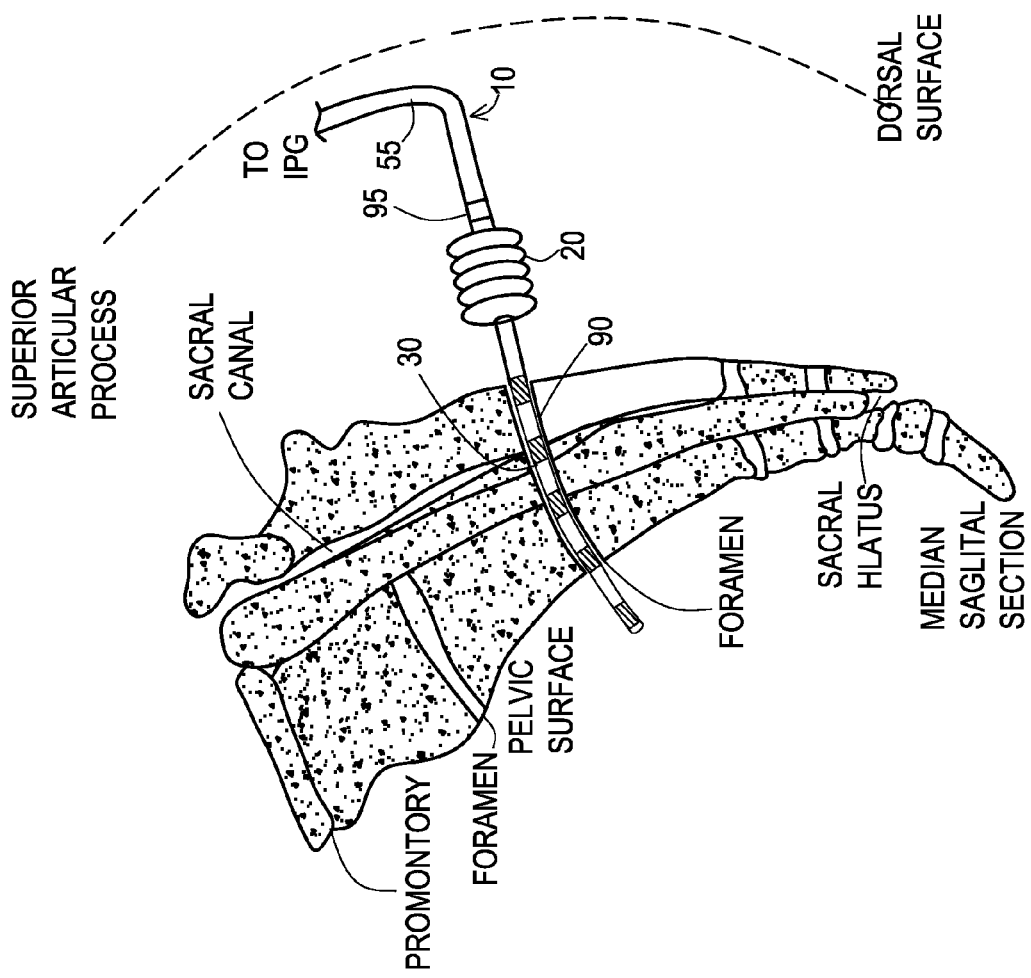

IMPLANTABLE MEDICAL ELECTRICAL STIMULATION LEAD FIXATION METHOD AND APPARATUS

FIELD OF THE INVENTION

This invention relates generally to device for electrical stimulation of body tissue. More specifically, this invention relates to an implantable medical electrical lead having at least one stimulation electrode and a fixation mechanism for fixing the lead within the tissue.

BACKGROUND OF THE INVENTION

Pelvic floor disorders such as, urinary incontinence, urinary urge/frequency, urinary retention, pelvic pain, bowel dysfunction (constipation, diarrhea), and erectile dysfunction, involve bodily functions that are influenced by the sacral nerves. Specifically, urinary incontinence is the involuntary control over the bladder that is exhibited in various patients. Urinary incontinence is primarily treated through pharmaceuticals and surgery. Many of the pharmaceuticals do not adequately resolve the issue and can cause unwanted side effects, and a number of the surgical procedures have a low success rate and are not reversible. Several other methods have been used to control urinary incontinence, for example, vesicostomy or an artificial sphincter implanted around the urethra. These solutions have drawbacks well known to those skilled in the art. In addition, the other mentioned disorders do not have adequate pharmaceutical or surgical treatment options.

The organs involved in bladder, bowel, and sexual function receive much of their control via the sacral nerves, in some instances the second, third, and fourth sacral nerves, commonly referred to as S2, S3 and S4 respectively. Electrical stimulation of these various nerves has been found to offer some control over these functions.

Neurostimulation leads with at least one stimulation electrode positioned on or near the sacral nerves of the human body have been implanted to provide partial control for urinary incontinence. Temporary sacral nerve stimulation is accomplished through implantation of a temporary neurostimulation lead extending through the skin and connected with a temporary external pulse generator as described for example in commonly assigned U.S. Pat. Nos. 5,957,965 and 6,104,960. A permanent neurostimulator can be implanted if the temporary stimulation is efficacious and it is possible to do so in the particular patient. Permanent implantation can be accomplished by implanting a permanent neurostimulation lead, extending the proximal portion of the lead body subcutaneously, and connecting its proximal end with an implantable pulse generator (IPG) implanted subcutaneously.

One problem that can be associated with implantation of both permanent and temporary neurostimulation leads involves maintaining the electrode(s) in casual contact, that is in a location where slight contact of the electrode with the sacral nerve may occur or in close proximity to the sacral nerve to provide adequate stimulation of the sacral nerve, while allowing for some axial movement of the lead body. In order to minimize the movement of the lead, the lead body is fixed to retard migration and dislodgement of the electrodes from the optimal position. This can be accomplished by employing sutures or a sacral lead fixation mechanism, an example of which is described in commonly assigned U.S. Pat. No. 5,484,445. An example of a lead that includes a fixation mechanism can be found in commonly assigned U.S. Pat. No. 6,999,819, the disclosure of which is incorporated herein by reference.

Although the fixation mechanisms of the above referenced patents are a significant advance over the prior art, there are still further advantages to be gained. Therefore, there remains a need for leads having other fixation mechanisms.

SUMMARY OF THE INVENTION

The invention includes a implantable medical electrical lead for electrical stimulation of body tissue that includes at least one electrode; a lead body; and at least one modifiable portion, wherein the at least one modifiable portion has a first configuration and a second configuration, wherein the first configuration exists when axial tension is exerted on the at least one modifiable portion, and wherein the second configuration exhibits a greater resistance to movement of the lead within the body tissue than does the first configuration.

The invention includes a kit that includes an implantable medical electrical lead for electrical stimulation of body tissue that includes at least one electrode; a lead body; at least one modifiable portion, wherein the at least one modifiable portion has a first configuration and a second configuration, wherein the first configuration exists when axial tension is exerted on the at least one modifiable portion, and wherein the second configuration exhibits a greater resistance to movement of the lead within the body tissue than does the first configuration; and an apparatus for applying axial tension on the at least one modifiable portion.

The invention also includes a medical electrical stimulation system that includes an implantable pulse generator for providing medical electrical stimulation; and an implantable medical electrical lead for electrical stimulation of body tissue that includes at least one electrode; a lead body; at least one modifiable portion wherein the at least one modifiable portion has a first configuration and a second configuration, wherein the first configuration exists when axial tension is exerted on the at least one modifiable portion, and wherein the second configuration exhibits a greater resistance to movement of the lead within the body tissue than does the first configuration.

The invention further includes a method of providing electrical stimulation of body tissue at a stimulation site employing an implantable pulse generator that includes the steps of providing an implantable medical lead that includes at least one electrode; a lead body; at least one modifiable portion wherein the at least one modifiable portion has a first configuration and a second configuration, wherein the first configuration exists when axial tension is exerted on the at least one modifiable portion, and wherein the second configuration exhibits a greater resistance to movement of the lead within the body tissue than does the first configuration; and at least one proximal connector element formed in a connector array in a proximal segment of the lead body; applying axial tension to at least the at least one modifiable portion; percutaneously introducing the implantable medical lead adjacent to the stimulation site; removing the axial tension to at least the at least one modifiable portion; and coupling the at least one proximal connector element with the implantable pulse generator.

The full range of advantages and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Embodiments of the invention are illustrated in the drawings, wherein like reference numerals refer to like elements in the various views. Furthermore, it will be understood by one of skill in the art that the drawings are not drawn to scale.

FIG. 8 is a cross-section view of the sacrum schematically illustrating a further step of implanting a lead of the invention subcutaneously routing the proximal portion of the lead body to the implantation site of the neurostimulator IPG.

DETAILED DESCRIPTION OF THE INVENTION

A lead in accordance with the invention can be utilized to provide neurostimulation or neuromodulation to any portion of the nervous system within the body of a patient. In one embodiment a lead in accordance with the invention can be utilized in any target tissue that requires some amount of fixation or traction to minimize movement of the lead. In one embodiment the lead can be implanted within muscle or connective tissue to stimulate or modulate peripheral nerves within that tissue.

A lead in accordance with the invention can be placed anywhere within the body where electrical stimulation is desired. In one embodiment a lead in accordance with the invention can be utilized to provide neurostimulation within the pelvic region of a patient. In such an embodiment the lead may be positioned to provide stimulation to one or more of the sacral nerves. Sacral nerves that may be stimulated using a lead in accordance with the invention include, but are not limited to the pudendal nerve, the pelvic splanchnic nerve, the cavernosa nerve in the penis or nerves located in or near the clitoris in a female, the hypogastric nerve, the vesicle nerve plexus, the perineal nerves, the pelvic nerve plexus, the prostate gland, the prostatic plexus nerve, the vagina, the anus, the urethra, the penis dorsal nerve, the inferior rectal nerves, the scrotal nerves, scrotum, Alcock's Canal, the sacro-tuberous ligament, the ischial tuberosity, the greater sciatic foramen, the lesser sciatic foramen, and other nerves or nerve portions located in the general region of the pelvic floor.

Neurostimulation using a lead in accordance with the invention can be utilized to treat any of a number of conditions including, but not limited to pelvic floor disorders such as urinary control disorders, fecal control disorders, sexual dysfunction, pelvic pain, interstitial cystitis, endometriosis, and genital pain such as vulvodynia or idiopathic chronic testicular pain. Although the invention is discussed with respect to stimulation of one or more nerves within the pelvic floor for the treatment of urinary incontinence, it will be understood by one of skill in the art, that leads of the invention can be utilized to treat other disorders or conditions by stimulating other nerves.

In one embodiment, a lead in accordance with the invention can be used with a therapy for treating urinary incontinence, such as MEDTRONIC INTERSTIM® Therapy. For example, an implantable neurostimulation system may stimulate organs involved in urinary, fecal or sexual function via C-fibers or sacral nerves at the second, third, and fourth sacral nerve positions, commonly referred to as S2, S3, and S4, respectively. In another embodiment a lead in accordance with the invention can be used with a therapy for treating gastroparesis, such as MEDTRONIC ENTERRA® Therapy.

Figure 1A:
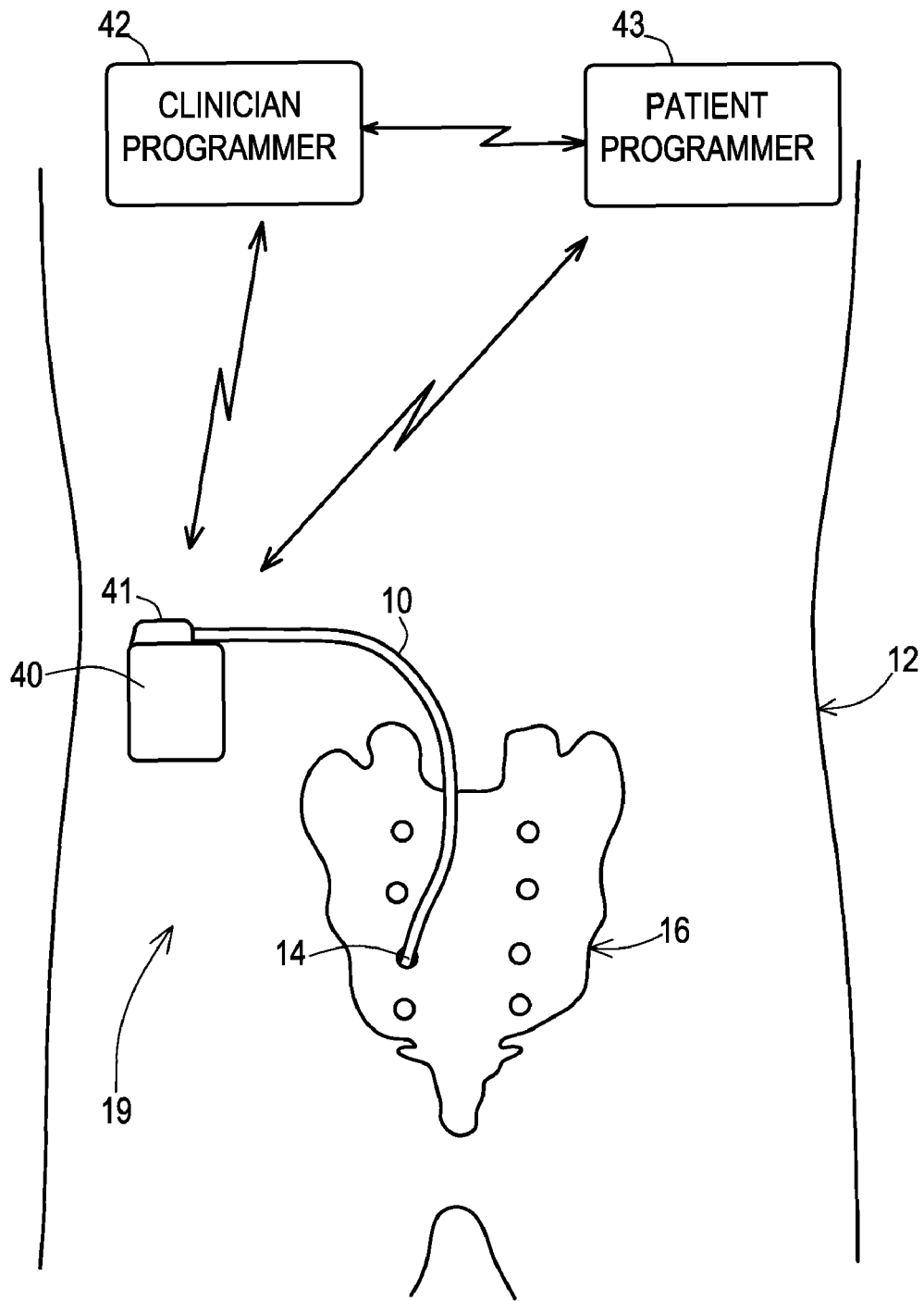
FIG. 1A is a diagram illustrating an implantable neurostimulator system for stimulating nerves, such as sacral nerves via a lead.

FIG. 1A is a diagram illustrating an implantable neurostimulation system 19 for stimulating a nerve, such as a sacral nerve, via lead 10. Lead 10 is generically depicted in FIG. 1A, and does not necessarily depict all of the features of a lead in accordance with the invention. Neurostimulation system 19 delivers neurostimulation to the sacral nerves or other regions of the nervous system known to treat pelvic floor disorders, urinary control disorders, fecal control disorders, interstitial cystitis, sexual dysfunction, and pelvic pain. Again, neurostimulation system 19 and lead 10 may be useful in other neurostimulation applications, such as spinal cord stimulation, deep brain stimulation, gastric stimulation, and the like. As shown in FIG. 1A, system 19 includes lead 10 and an implantable neurostimulator 40. In addition, a proximal end 32 of stimulation lead 10 may be coupled to a connector block 41 associated with neurostimulator 40. The lead 10 also has a distal end 31 (not visible in FIG. 1A, but seen in FIGS. 1B, 1C, and 1D).

Neurostimulator 40 includes an implantable pulse generator, and delivers neurostimulation therapy to patient 12 in the form of electrical pulses generated by the implantable pulse generator. In the example of FIG. 1A, neurostimulator 40 is implanted in the upper left buttock of patient 12, but may be implanted at other locations. An example of a commercially available neurostimulator includes, but is not limited to MEDTRONIC® Model 3023 Neurostimulator.

Lead 10 carries one or more stimulation electrodes, for example, 1 to 8 electrodes, to permit delivery of electrical stimulation to sacral nerves. Embodiments of the invention may have 1, 2, 3, 4, 5, 6, 7, 8 or more electrodes. The at least one electrode 30 can include ring electrodes, coil electrodes, circumferential segment electrodes, or any combination thereof. One embodiment of a lead in accordance with the invention has at least two (2) electrodes. Another embodiment of a lead in accordance with the invention has at least four (4) electrodes. In one embodiment having at least four electrodes, at least one of those electrodes can be a coil electrode. In another embodiment of the invention having at least four electrodes, at least one electrode is a coil electrode and at least one of the other electrodes is a ring electrode.

The at least one electrode 30 can be made of any commonly utilized material as is known to those of skill in the art. In one embodiment the at least one electrode 30 is made of a solid surface, bio-compatible material, examples of such materials include, but are not limited to, platinum, a platinum-iridium alloy, or stainless steel for example. Also, in some embodiments, lead 10 may carry one or more electrodes capable of sensing one or more parameters to permit neurostimulator 40 to sense electrical signals within sacrum 16, for example. In some embodiments, neurostimulator 40 may be coupled to two or more leads deployed at different positions, for example, relative to the spinal cord or sacral nerves.

In one embodiment lead 10 includes a lead body that contains one or more conductors to electrically couple the one or more electrodes to terminals within neurostimulator 40. In one embodiment the outer diameter of the lead body, referred to herein as the lead body diameter can be from about 0.5 mm to about 2 mm. In yet another embodiment, the lead body diameter can be about 1 mm to about 1.5 mm. In a further embodiment the lead body diameter can be about 1.3 mm.

Leads in accordance with the invention can have variable lengths, depending at least in part on considerations such as the type of tissue that the lead is to be implanted in, the surrounding anatomy where the lead will be implanted, the particular configuration of the lead, the number of modifiable portions within the lead, the number of electrodes within the lead, the location of the one or more modifiable portions and/or the one or more electrodes within the lead, whether or not the lead will be used with an extension, and where the neurostimulator is to be implanted, for example.

In one embodiment of the invention, where the lead is to be used for stimulation of the pelvic floor with a lead extension, the length of the lead can range from about 10 cm to about 100 cm. In another embodiment of the invention, where the lead is to be used for stimulation of the pelvic floor with a lead extension, the length of the lead can range from about 10 cm to about 80 cm. In yet another embodiment of the invention, where the lead is to be used for stimulation of the pelvic floor with a lead extension, the length of the lead can range from about 20 cm to about 60 cm.

Figure 1B:
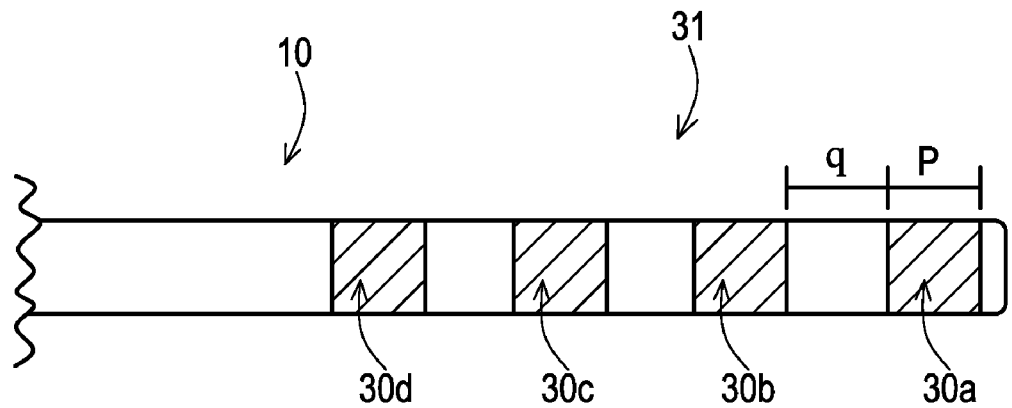
FIG. 1B is a diagram illustrating a portion of a lead in accordance with the invention.

In one embodiment, the at least one electrode 30 is located towards the distal end 31 of the lead 10. FIG. 1B depicts a portion of an exemplary lead 10 in accordance with the invention. The exemplary lead 10 depicted there includes four electrodes 30a, 30b, 30c, and 30d. The electrodes 30a, 30b, 30c, and 30d have an electrode length p. In this example, the four electrodes 30a, 30b, 30c, and 30d have equal electrode lengths p. One of skill in the art, having read this specification, will understand that the electrode lengths p could be different or the same. One of skill in the art will also understand that the electrode lengths p of any one electrode or all of the electrodes can vary and may be at least in part dependent on a number of factors including, but not limited to, the type of tissue that the lead will be implanted in, the surrounding anatomy where the lead will be implanted, the stimulation parameters that the lead will be delivering, the types of electrodes, and the number of electrodes.

In one embodiment, the electrode length p can range from about 1 mm to about 20 mm. In another embodiment the electrode length p can range from about 1 mm to about 3 mm. In yet another embodiment the electrode length p can range from about 3 mm to about 10 mm. In one embodiment, a lead 10 has at least one electrode that has an electrode length p of about 3 mm. In another embodiment, a lead 10 has at least one electrode that has an electrode length p of about 10 mm.

The electrodes 30a, 30b, 30c, and 30d are separated by inter-electrode distances q. In this example, the four electrodes 30a, 30b, 30c, and 30d are separated by equal inter-electrode distances q, but one of skill in the art, having read this specification, will understand that the inter-electrode distances q could be different. One of skill in the art, having read this specification, will also understand that the inter-electrode distances q of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the inter-electrode distances q can range from about 0.5 mm to about 5 mm. In another embodiment the inter-electrode distances q can range from about 1 mm to about 2 mm. In yet another embodiment the inter-electrode distances q can range from about 1.2 mm to about 1.6 mm. In one embodiment, a lead 10 has at least two electrodes that have an inter-electrode distance q of about 1.5 mm. In another embodiment, a lead 10 has at least two electrodes that have an inter-electrode distance q of about 3 mm.

Figure 1C:
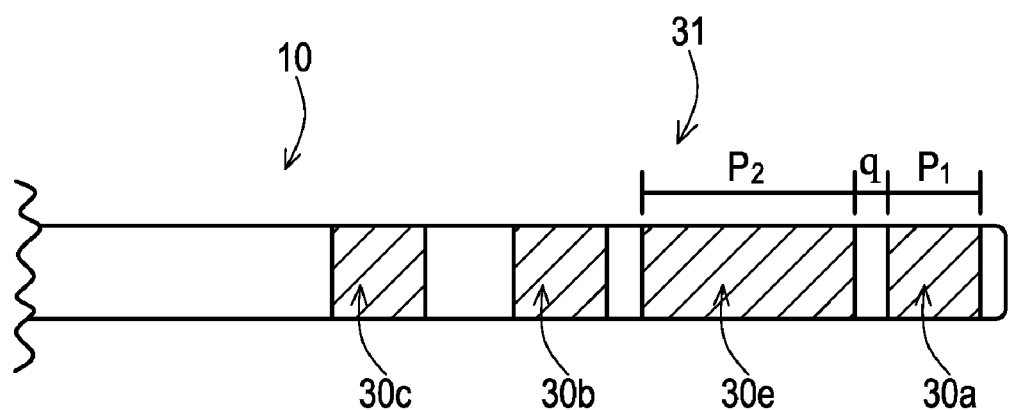
FIG. 1C is a diagram illustrating a portion of a lead in accordance with the invention.

The exemplary lead depicted in FIG. 1C also includes four electrodes 30a, 30b, 30c, and 30e in which only three of the electrodes 30a, 30b, and 30c have the same electrode lengths $p_1$, and the fourth electrode 30e has a different electrode length $p_2$. One of skill in the art, having read this specification, will understand that any combination of equal and unequal electrode lengths $p_1$-$p_2$ are included within the scope of this invention. In one embodiment of the invention, a lead includes four ring electrodes with the same electrode lengths p. In another embodiment of the invention, a lead includes three ring electrodes with the same electrode lengths p and one coil electrode with a different electrode length p.

The at least one electrode can be electrically coupled to the distal end of a coiled wire lead conductor within the body of the lead. The proximal ends of the separately insulated lead conductors can each be coupled to respective connector elements, for example ring-shaped connector elements, in a proximal connector element array in the body of the lead. In one embodiment, the conductor wires can be formed of an MP35N alloy and are insulated from one another within an insulating polymer sheath such as polyurethane, fluoropolymer or silicone rubber for example. The lead conductor wires can be separately insulated by an insulation coating and can be wound in a quadra-filar manner having a common winding diameter within the outer sheath. The coil formed by the coiled wire conductors defines a lead body lumen of the lead body. It will be understood that a further inner tubular sheath could be interposed within the aligned wire coils to provide the lead body lumen.

The connector elements can be adapted to be coupled with a neurostimulator IPG, additional intermediate wiring, or other stimulation device adapted to be implanted subcutaneously. An example of such an implantable pulse generator is the MEDTRONIC® Neurostimulator Model 3023. Electrical stimulation pulses generated by the neurostimulator IPG are applied to a nerve or nerves, such as the sacral nerve, through the at least one electrode in either a unipolar or bipolar stimulation mode.

As further shown in FIG. 1A, implantable neurostimulation system 19 also may include a clinician programmer 42 and a patient programmer 43. Clinician programmer 42 may be a handheld computing device that permits a clinician to program neurostimulation therapy for patient 12, e.g., using input keys and a display. For example, using clinician programmer 42, the clinician may specify neurostimulation parameters for use in delivery of neurostimulation therapy.

Clinician programmer 42 supports radio frequency telemetry with neurostimulator 40 to download neurostimulation parameters and, optionally, upload operational or physiological data stored by neurostimulator. In this manner, the clinician may periodically interrogate neurostimulator 40 to evaluate efficacy and, if necessary, modify the stimulation parameters.

Like clinician programmer 42, patient programmer 43 may be a handheld computing device. Patient programmer 43 may also include a display and input keys to allow patient 12 to interact with patient programmer 43 and implantable neurostimulator 40. In this manner, patient programmer 43 provides patient 12 with an interface for control of neurostimulation therapy by neurostimulator 40.

For example, patient 12 may use patient programmer 43 to start, stop or adjust neurostimulation therapy. In particular, patient programmer 43 may permit patient 12 to adjust stimulation parameters such as duration, amplitude, pulse width and pulse rate, within an adjustment range specified by the clinician via clinician programmer 42.

Neurostimulator 40, clinician programmer 42 and patient programmer 43 may communicate via wireless communication, as shown in FIG. 1A. Clinician programmer 42 and patient programmer 43 may, for example, communicate via wireless communication with neurostimulator 40 using RF telemetry techniques known in the art. Clinician programmer 42 and patient programmer 43 also may communicate with each other using any of a variety of local wireless communication techniques, such as RF communication according to the 802.11 or Bluetooth specification sets, or other standard or proprietary telemetry protocols.

Figure 1D:
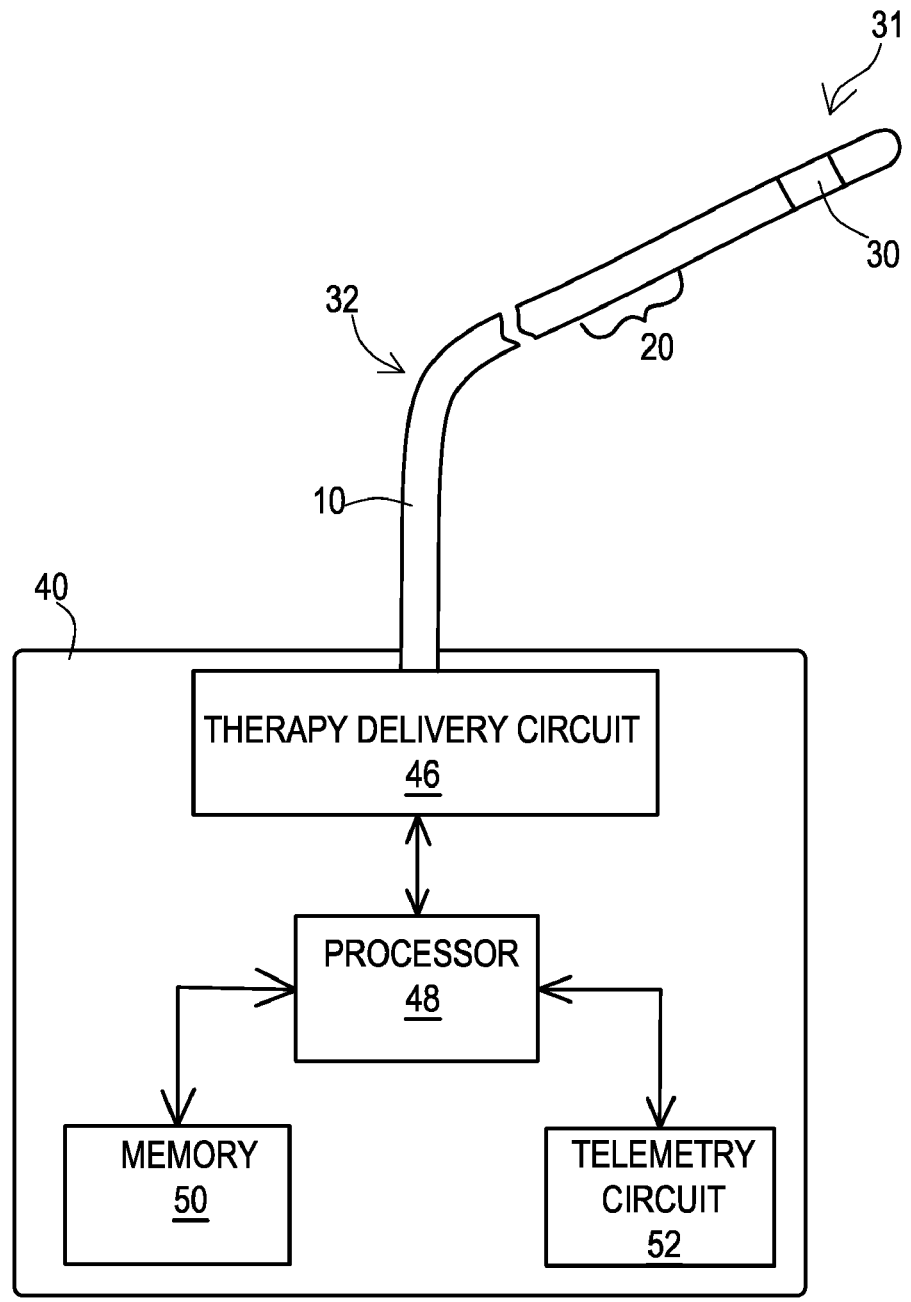
FIG. 1D is a block diagram illustrating various components of an implantable neurostimulator with an implantable lead incorporating a fixation mechanism.

FIG. 1D is a block diagram illustrating various components of an implantable neurostimulator 40 incorporating an implantable lead 10 with a modifiable portion 20. As shown in FIG. 1D, neurostimulator 40 delivers neurostimulation therapy via at least one electrode 30 of lead 10. Electrode 30 is electrically coupled to a therapy delivery circuit 46 via conductors within lead 10. Therapy delivery circuit 46 may, for example, include an implantable pulse generator coupled to a power source such as a battery. The implantable pulse generator within therapy delivery circuit 46 delivers electrical pulses to patient 12 via the at least one electrode 30 under the control of a processor 48.

Processor 48 controls the implantable pulse generator within therapy delivery circuit 46 to deliver neurostimulation therapy according to selected stimulation parameters. In one embodiment, processor 48 can control therapy delivery circuit 46 to deliver electrical pulses with selected amplitudes, pulse widths, rates, or some combination thereof as specified by the program(s). In addition, processor 48 can also control therapy delivery circuit 46 to deliver the neurostimulation pulses via selected subsets of one or more electrodes 30 with selected polarities.

Processor 48 may control therapy delivery circuit 46 to deliver each pulse according to a different program, thereby interleaving programs to simultaneously treat different symptoms or provide a combined therapeutic effect. For example, in addition to treatment of one symptom such as sexual dysfunction, neurostimulator 40 may be configured to deliver neurostimulation therapy to treat other symptoms such as pain or incontinence. Processor 48 may include a microprocessor, a controller, a digital signal processor (DSP), an application-specific integrated chip (ASIC), a field-programmable gate array (FPGA), discrete logic circuitry, or the like.

Neurostimulator 40 also includes a memory 50. In some embodiments, memory 50 stores multiple sets of stimulation parameters that are available to be selected by patient 12 for delivery of neurostimulation therapy to the patient 12. For example, memory 50 may store stimulation parameters transmitted by clinician programmer 42.

Memory 50 also stores program instructions that, when executed by processor 48, cause neurostimulator 40 to deliver neurostimulation therapy. Memory 50 may include any volatile or non-volatile media, such as random access memory (RAM), random read-only memory (ROM), compact disc-read-only memory (CD-ROM), non-volatile random access memory (NVRAM), electrically erasable programmable read-only memory (EEPROM), flash memory, and the like. Accordingly, computer-readable media storing instructions may be provided to cause processor 48 to provide functionality as described herein.

In some embodiments a telemetry circuit 52 can support wireless communication between two or more of neurostimulator 40, clinician programmer 42, and patient programmer 43. In addition, in some embodiments, telemetry circuit 52 supports wireless communication with one or more wireless sensors that sense physiological signals and transmit the signals to neurostimulator 40 clinician programmer 42, patient programmer 43 or some combination thereof.

As mentioned above, migration of lead 10 can have detrimental effects on the efficacy of neurostimulation therapy for a patient 12. Fixing the neurostimulation lead 10 to surrounding tissue may prevent harmful effects that may result from a loose neurostimulation lead 10. As described below, a lead in accordance with the invention may provide fixation (not shown in FIGS. 1A through 1D) between the lead 10 and tissue surrounding the lead 10, such as tissue within the sacrum 16, without the need for surgical implantation techniques, such as sutures.

Leads in accordance with the invention can be utilized for electrical stimulation of body tissue and include at least one modifiable portion, that has a first configuration and a second configuration wherein the first configuration exists when axial tension is exerted on the modifiable portion, and wherein the second configuration of the modifiable portion exhibits a greater resistance to movement of the lead within the body tissue than does the first configuration. The second configuration generally provides increased resistance to movement of the lead within the body tissue because of its larger size and/or increased surface area that interacts with the surrounding tissue.

In one embodiment, the first configuration of the modifiable potion is coaxial with and has substantially the same diameter and configuration as an adjacent portion of the lead body. In another embodiment the modifiable portion is formed from the same kind but a different piece of material, and in yet another embodiment the modifiable portion is formed from a different kind of material. In such embodiments the modifiable portion can be secured to the remainder of the lead body as would be known to one of skill in the art, having read this specification. In one embodiment of the invention, the modifiable portion may be an integral portion of the lead body, for example of the insulation of the lead body. In yet another embodiment, the modifiable portion may be a component that interfaces with the lead body, for example the insulation of the lead body, at the desired location. The modifiable portion may be made, for example, molded, from any biocompatible polymer such as silicone or polyurethane for example and joined to the lead body with suitable medical grade adhesives. Other methods, as would be known to those of skill in the art, having read this specification could also be utilized.

Both the modifiable portion and the lead body have diameters, referred to herein as the modifiable portion diameter and the lead body diameter respectively. The lead body diameter is generally considered as the diameter of the lead body directly adjacent to the modifiable portion. In one embodiment of the invention, the diameter of the first configuration of the modifiable portion and the lead body diameter are substantially equal. In another embodiment, the diameter of the first configuration of the modifiable portion diameter is less than the lead body diameter. The diameter of the second configuration is greater than the lead body diameter. In one embodiment, the diameter of the second configuration is at least about 50% bigger than the lead body diameter. In another embodiment, the diameter of the second configuration is at least about 100% bigger than the lead body diameter. In yet another embodiment, the diameter of the second configuration is at least about 150% bigger than the lead body diameter.

Figure 2A:
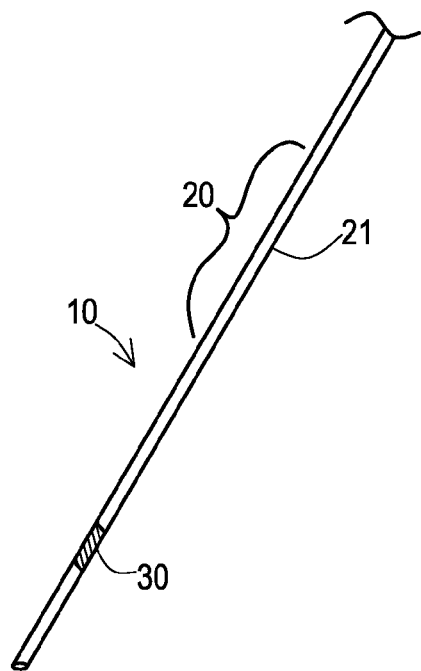
FIG. 2A is an exemplary embodiment of a portion of a lead in accordance with the invention while the modifiable portion is in a first configuration.
Figure 2B:
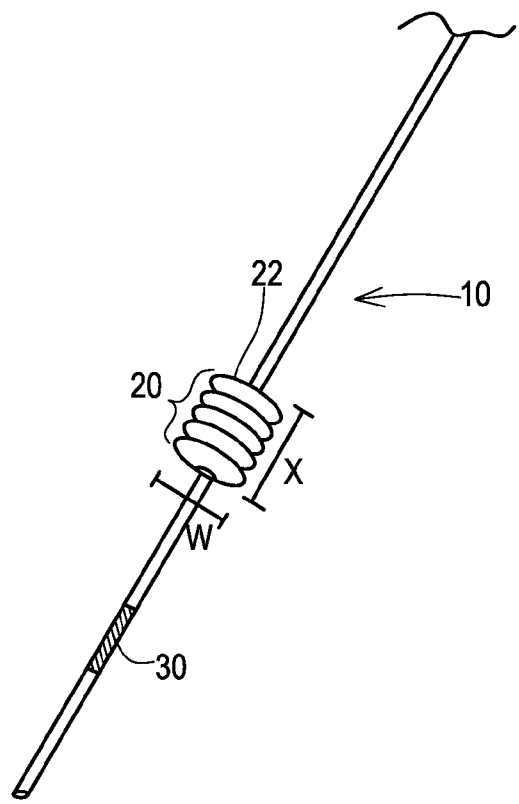
FIG. 2B is the lead depicted in FIG. 3A while the modifiable portion is in an second configuration.

FIGS. 2A and 2B offer an example of a lead 10 exhibiting a first configuration (FIG. 2A) and exhibiting a second configuration (FIG. 2B). As seen there, the modifiable portion 20 goes from a substantially straight configuration 21 to a bellowed configuration 22 after the axial tension is released from the modifiable portion.

The modifiable portion has a width when the axial tension is released. The width is depicted as the dimension w in FIG. 2B. In one embodiment of the invention, the width w of the modifiable portion can range from about 2 mm to about 8 mm. In another embodiment the width w of the modifiable portion can range from about 3 mm to about 6 mm. In yet another embodiment the width w of the modifiable portion can range from about 3 mm to about 4 mm. In another embodiment of the invention, the width w of the modifiable portion can be about 3 times the diameter of the lead body at an area adjacent the modifiable portion.

The modifiable portion can be described as being made up of one or more bellows. As depicted in FIG. 2B, one bellows has a length z from the outer most portion of one bellow to the outermost portion of another bellow, when there is no axial tension being exerted on the modifiable portion. In one embodiment, the length of one bellow, z, can range from about 2 mm to about 8 mm. In another embodiment, the length of one bellow, z, can range from about 3 mm to about 6 mm. In yet another embodiment the length of one bellow can range from about 3 mm to about 4 mm. In another embodiment of the invention, the length of one bellow, z, can approximate the width of the modifiable portion, w.

The modifiable portion can be described as comprising a number of individual bellows. In one embodiment, a modifiable portion can have from about 1 to about 10 bellows. In another embodiment a modifiable portion can have from about 2 to about 8 bellows. In yet another embodiment, a modifiable portion can have from about 4 to about 5 bellows. The example depicted in FIG. 2B is a modifiable portion having about 5 bellows.

The modifiable portion has an overall length when the axial tension is released. The overall length is depicted as the dimension x in FIG. 2B. In one embodiment of the invention, the length x of the modifiable portion can range from about 4 mm to about 25 mm. In another embodiment of the invention, the overall length x of the modifiable portion can range from about 5 mm to about 15 mm. In yet another embodiment of the invention, the overall length x of the modifiable portion can range from about 8 mm to about 12 mm.

As will be understood by one of skill in the art, having read this specification, the width of the modifiable portion, w; the length of individual bellows, z; the number of individual bellows, and the overall length of the modifiable portion can all vary based on the other dimensions and numbers as well as the portion of the body where the lead is to be implanted, the particular anatomy of where the lead is to be implanted, and the particular type of tissue that the lead is to be implanted into.

In one embodiment of the invention, the modifiable portion is made of one or more materials that are capable of being axially tensioned to maintain the first configuration but regains its second configuration when the axial tension is released. In one embodiment the modifiable portion is made of an elastomeric material that is biocompatible. Examples of materials that can be used to make the at least one modifiable portion include, but are not limited to, silicone, and polyurethane. In one embodiment, the at least one modifiable portion is made of silicone.

The modifiable portion has a first configuration and an second configuration. The modifiable portion is transitioned from the first configuration to the second configuration via introduction of an axial tensioning means. The tensioning means can include an internal stylet or an external sheath.

In one embodiment, the external force is provided via a sheath. In one embodiment, the sheath can be configured to cover less than the entire modifiable portion, but enough of the modifiable portion to apply sufficient axial tension to maintain the modifiable portion in it's first configuration when it is placed on the outside of the modifiable portion. In another embodiment, the sheath can be configured to cover at least all of the modifiable portion. In yet another embodiment, the sheath covers more of the lead than just the modifiable portion. One of skill in the art would therefore understand, having read this specification, that the dimensions of the sheath would depend at least in part on the dimensions of the modifiable portion and the lead body.

In an embodiment of the invention where a sheath provides the axial tension, the sheath can be made of any material with enough strength to stretch the modifiable portion into its first configuration. In one embodiment, a sheath can be made of a metal, such as stainless steel, or plastic for example.

In one embodiment of the invention that is designed to be used for implantation within the pelvic floor for sacral nerve stimulation, the lead may be configured so that the second configuration lies in close proximity to the foramen after the lead is implanted. In another embodiment of the invention that is designed to be used for implantation within the pelvic floor for sacral nerve stimulation, the lead may be configured so that the second configuration forms within the foramen. Such a lead could allow the second configuration to act against the bone and the inside of the foramen, or on either side of the facial layer covering the foramen to further anchor the lead where it is implanted.

Figure 3A:
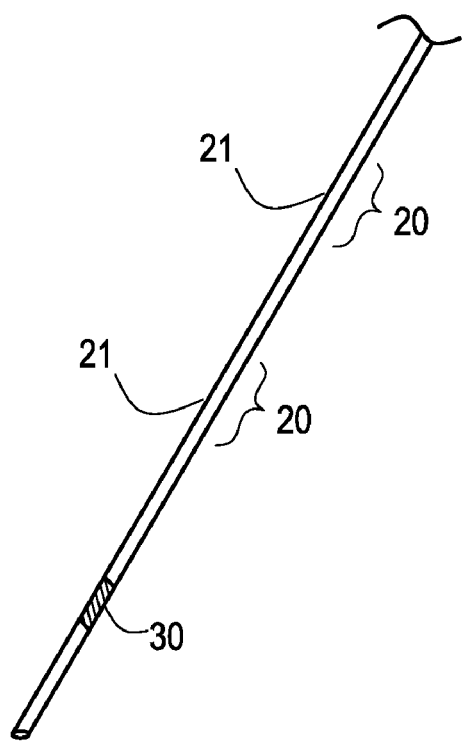
FIG. 3A is an exemplary embodiment of a portion of a lead in accordance with the invention while the two modifiable portions are in first configurations.
Figure 3B:
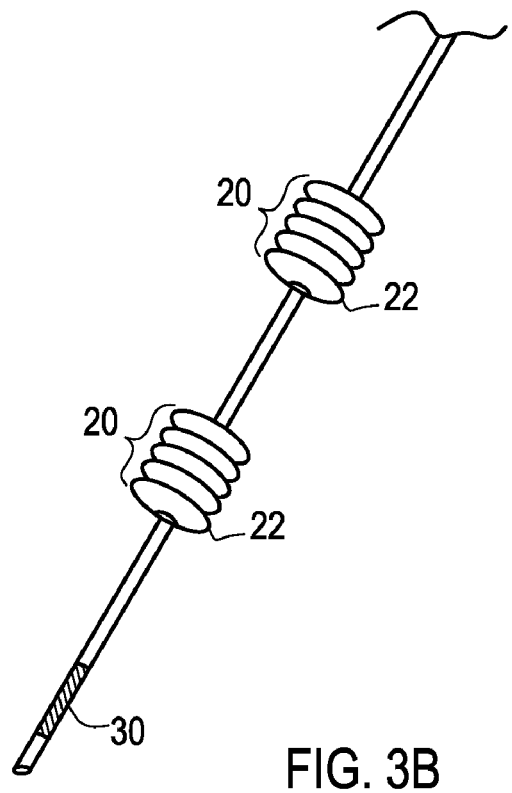
FIG. 3B is the lead depicted in FIG. 3A while the modifiable portions are in second configurations.

FIGS. 3A and 3B offer another example of a lead 10 exhibiting two modifiable portions in first configurations (FIG. 3A) and second configurations (FIG. 3B).

Figure 4:
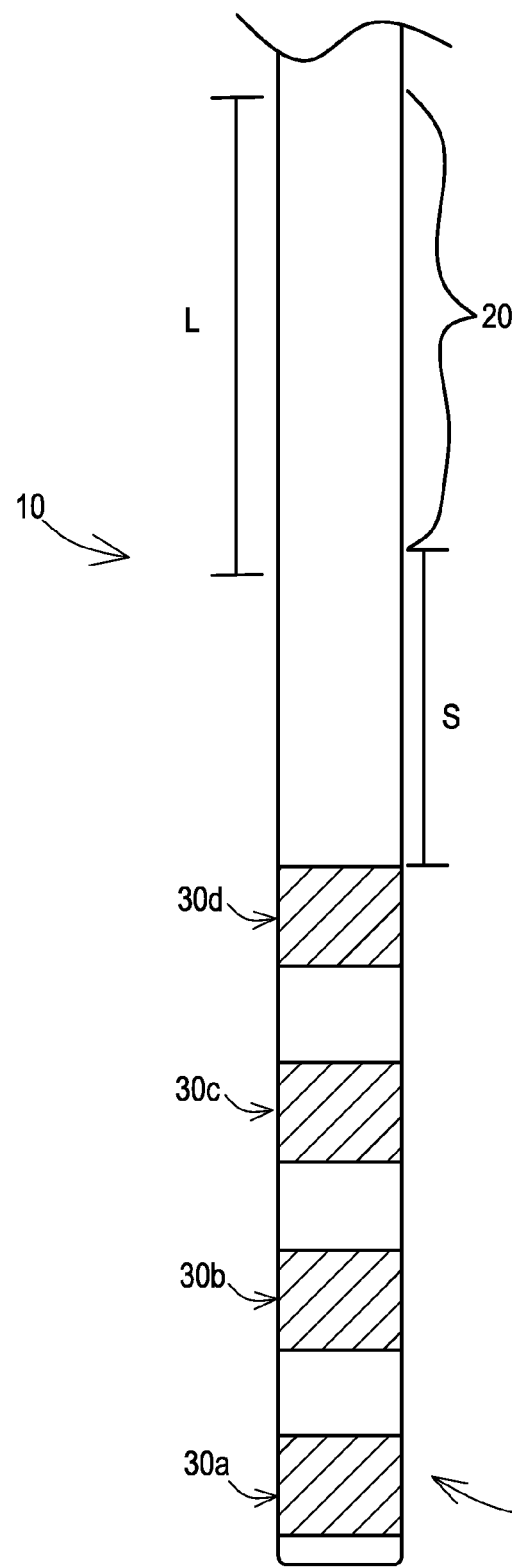
FIG. 4 is a diagram illustrating a portion of a lead in accordance with the invention.

FIG. 4 depicts another exemplary embodiment of a lead 10 in accordance with the invention. As seen in FIG. 4, a lead 10 in accordance with the invention has a spacer distance s between the modifiable portion and the most proximal electrode. In leads having more than one modifiable portion, the spacer distance s between the most proximal electrode and the first modifiable portion and the spacer distance s between the first modifiable portion and the second modifiable portion need not, but can be the same. One of skill in the art, having read this specification will understand that whether or not the spacer distances s are the same, can depend at least in part on considerations such as, the type of tissue that the lead is to be implanted in, the surrounding anatomy where the lead will be implanted, the particular configuration of the second configuration of the modifiable portion, the number of modifiable portions within the lead, and the location of the at least one modifiable portion within the lead.

In one embodiment, spacer distance s can range from about 1 mm to about 20 mm. In another embodiment, spacer distance s can range from about 5 to about 15 mm. In yet another embodiment, spacer distance s is about 10 mm. One of skill in the art, having read this specification, will understand that any particular spacer distance s can vary depending at least in part on considerations such as, the type of tissue that the lead is to be implanted in, the surrounding anatomy where the lead will be implanted, the particular configuration of the second configuration of the modifiable portion, the number of modifiable portions within the lead if there is more than one, and the location of the one or more modifiable portions within the lead.

As described above, a lead 10 may include at least one modifiable region 20 to fix the lead in any tissue surrounding the lead, such as tissue within an epidural region or tissue within or near a foramen 14 of sacrum 16 for example. At least one modifiable region 20 may be located between electrodes 30 at a distal end of lead 10, or at a proximal end of lead 10. In one embodiment, at least one modifiable region 20 may be disposed proximal to the electrode 30 near the distal end 31 of lead 10 in order to fix the electrodes in place relative to a target stimulation site. In one embodiment, a lead in accordance with the invention may have more than one modifiable region 20. In one embodiment of the invention, a lead of the invention may have 1, 2, 3, 4, or more modifiable regions.

When manufacturing a lead in accordance with this invention, the lead body, including the one or more electrode(s), the one or more modifiable portion(s), and any other features of the lead can be manufactured as was known to one of skill in the art, having read this specification, at the time of the invention.

FIGS. 5-8 depict the primary steps of implanting the sacral nerve stimulation lead 10 of the invention. An introducer 200 receives the distal portion 31 of the lead including the at least one electrode 30 and the at least one modifiable portion disposed within the lumen of the introducer 200. In one embodiment the at least one modifiable portion is subjected to axial tension via the introducer 200. As the lead is introduced into the introducer 200, the geometry of the modifiable portion is elongated and made coaxial with the lead body by the inner diameter of the introducer 200. In one embodiment of the invention, the lead conductors that are housed inside the lead body may be made of coils that can easily accommodate an increase in length.

In another embodiment of the invention, the at least one modifiable portion is subjected to axial tension via a stylet 100 disposed within the lead body lumen. The internal stylet can also function to make it easier to push the lead through the tissue that it is being implanted into.

Figure 5:
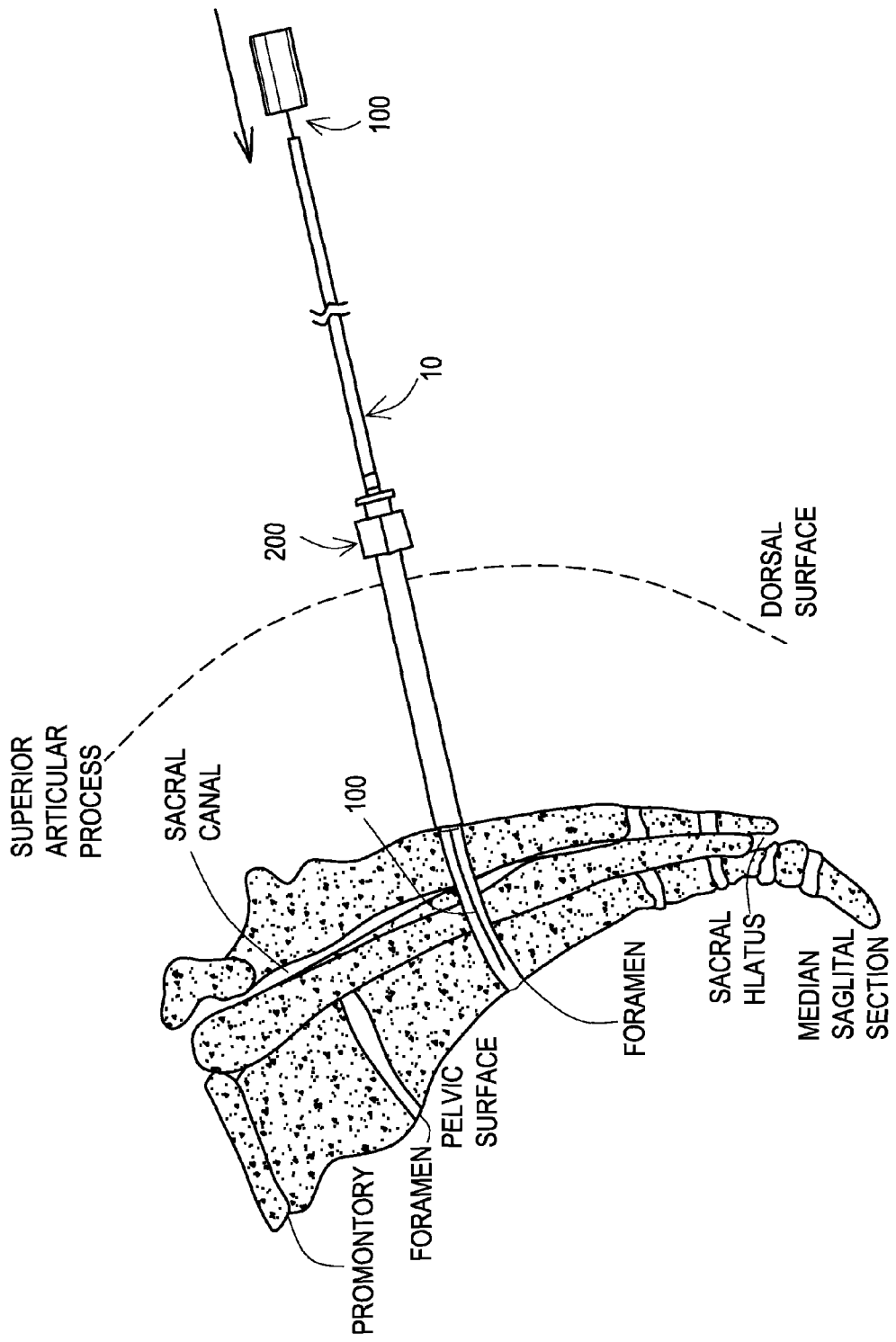
FIG. 5 is a cross-section view of the sacrum schematically illustrating an initial step of implanting a lead of the invention with the modifiable portion of the lead exposed to a first temperature.
Figure 6:
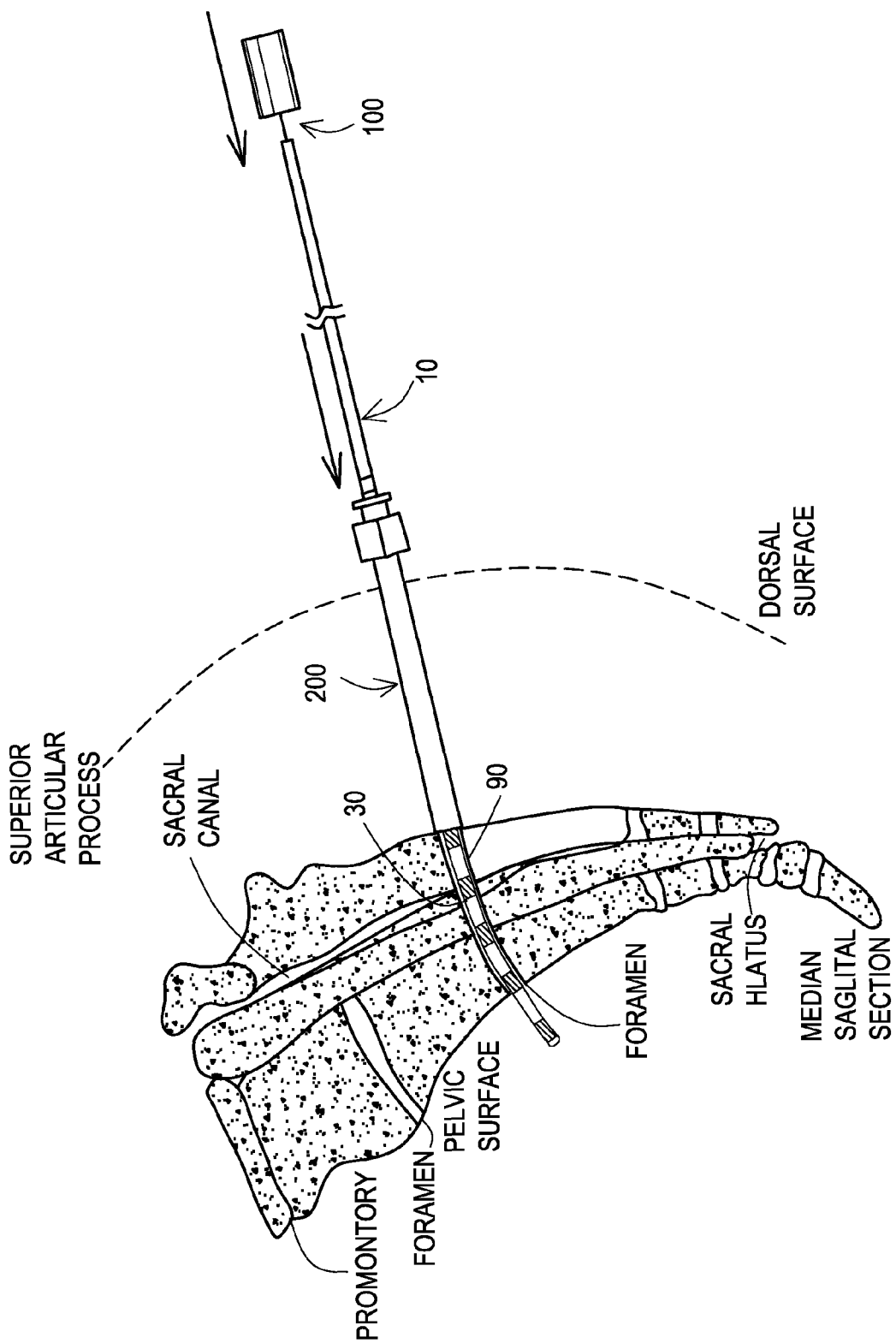
FIG. 6 is a cross-section view of the sacrum schematically illustrating a further step of implanting a lead of the invention extending the one or more electrodes through a foramen.

The assembly can be advanced percutaneously at a selected angle until the introducer distal end is disposed at the selected foramen as shown in FIG. 5.

The advancement of the introducer 200 can be accomplished separately over a guide wire previously percutaneously advanced from the skin incision into the foramen to establish the angle of advancement. Also, a two-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately provides the introducer 200 in the location depicted in FIG. 5.

To determine the best location of the one or more electrodes, an insulated needle with both ends exposed for electrical stimulation can be used to locate the foramen and locate the sacral nerve by applying electrical stimulation through the needle using an external pulse generator. The efficacy of the location is tested by evaluating the physiologic response in relation to the electrical threshold energy required to elicit the response. For control of urinary incontinence, the physician can implant the medical electrical lead 10 near the S3 sacral nerves. The implantable medical electrical lead 10 may, however, be inserted near any of the sacral nerves including the S1, S2, S3, or S4, sacral nerves accessed via the corresponding foramen depending on the necessary or desired physiologic response.

Figure 7:
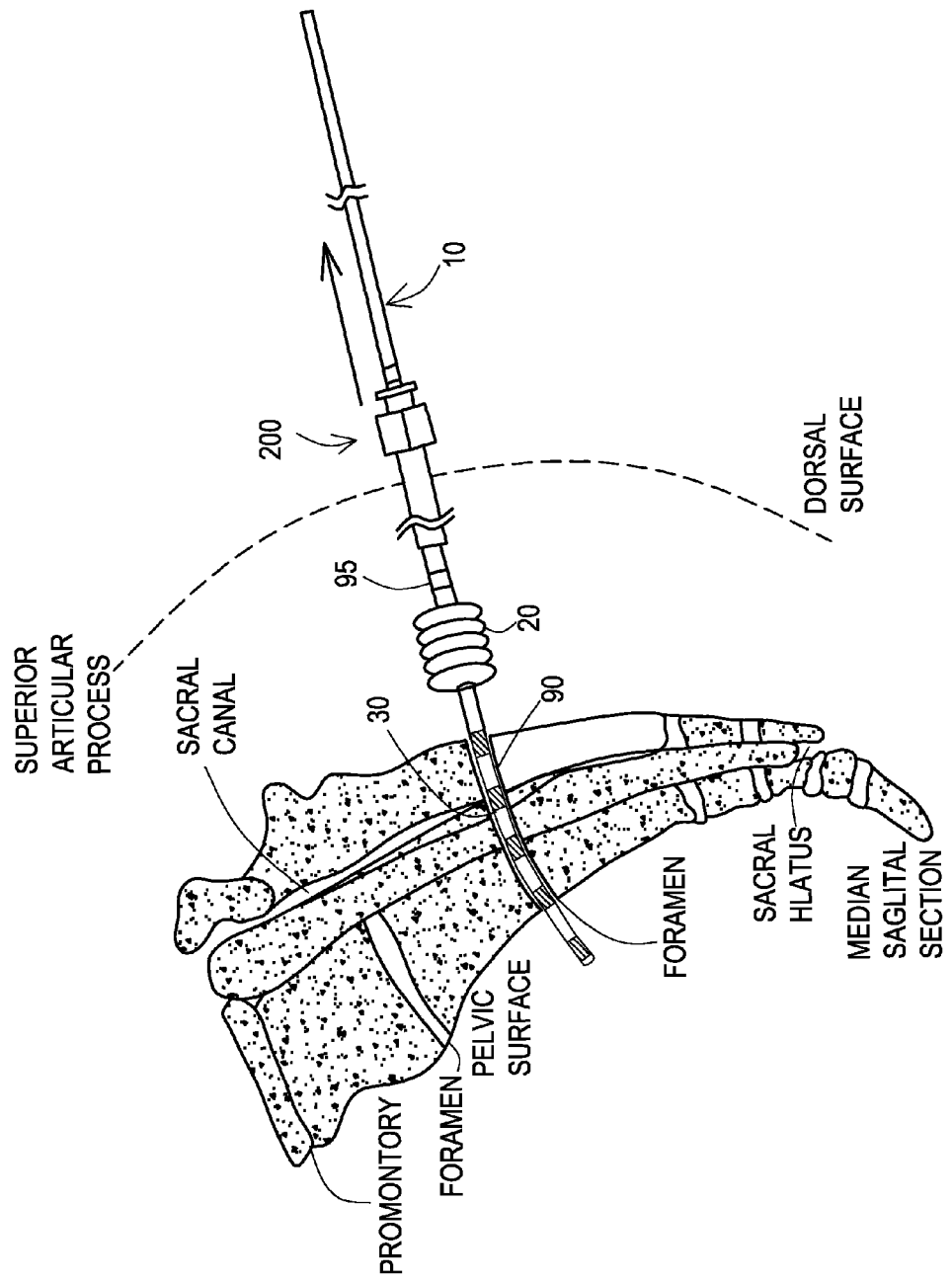
FIG. 7 is a cross-section view of the sacrum schematically illustrating a further step of implanting a lead of the invention retracting the introducer and after the axial tension was released from the modifiable portion.

After electrical testing to establish optimal positioning is completed the introducer 200 is retracted proximally or the internal stylet is removed to release the axial tensioning on the modifiable portion. In one embodiment, the stylet 100 can be held in position while the introducer 200 is removed; this should maintain electrode position and still allow the modifiable portion to transition as the introducer is removed. The at least one modifiable portion 20 is now transitioned from the first configuration to the second configuration. The introducer 200 and internal stylet 100, if present, are completely removed from the modifiable portion, as shown in FIG. 7. As shown in FIG. 8, the proximal portion 55 of the lead 10 is bent laterally with respect to the distal portion of the lead 10 and implanted through a subcutaneously tunneled path to the neurostimulator IPG.

The lead 10 of the invention also offers the possibility of transitioning the modifiable portion 20 back into the first configuration and repositioning the lead 10 within the patient. To do this, the axial tension is again provided to the modifiable portion of the lead to transition the modifiable portion back to the first configuration. The lead can then easily be repositioned and the axial tension can be released to transition the modifiable portion into the second configuration again. Such a sequence of steps could also be utilized if or when the lead 10 is to be permanently removed. Returning the modifiable portion of the lead 10 to its first configuration may decrease damage to surrounding tissue when the lead is removed.

In one embodiment of the invention, a lead 10 can include one or more markers, of which marker 90 is an example. Such markers can be made of materials that can be visualized under fluoroscopy. This can allow the physician to more easily see where the particular parts of the lead 10 are within the patient. For example, a lead that has a first marker 90 on the distal end of a modifiable portion 20 and a second marker 95 (as seen in FIGS. 7 and 8) on the proximal end of the modifiable portion, can allow the position of the modifiable portion 20 to be easily located within the patient. When the modifiable portion 20 transitions into the second configuration, it bears against the tissue and inhibits proximal retraction of the lead body through the subcutaneous tissue if traction is applied to the lead body since the second configuration resists inversion, migration, retraction, and displacement in the proximal direction. Leads in accordance with the invention can also provide strain relief between proximal forces (or strains) in the lead body and the desired location of the electrodes.

The medical electrical leads and procedures of the present invention can be used to stimulate multiple nerves or multiple sides of a single nerve bundle. It should also be understood that although sacral nerve stimulation was exemplified herein, the leads of the invention can be used for other types of nerve stimulation. In addition, the medical electrical lead 10 can also be used as an intramuscular lead where the at least one modifiable portion can engage against muscle and assist in preventing dislodgement of the at least one electrode. This may be useful in muscle stimulation such as dynamic gracilo-plasty or stomach stimulation for gastroparesis or obesity.

Although the invention has been described in detail with particular reference to a certain embodiments thereof, it will be understood variations and modifications can be effected within the scope of the following claims. Such modifications may include substituting elements or components which perform substantially the same function in substantially the same way to achieve substantially the same result for those described herein.

We claim:

1. An implantable medical electrical lead for electrical stimulation of body tissue comprising:
   at least one electrode;
   a lead body; and
   at least one modifiable portion joined to the lead body wherein the at least one modifiable portion has a first configuration and a second configuration, wherein the first configuration exists when axial tension is exerted only on an exterior surface of the at least one modifiable portion by contact on the exterior surface from a separate body, wherein the at least one modifiable portion transitions from the first configuration to the second configuration by removal of the contact by the separate body to release the axial tension, and wherein the second configuration exhibits a greater resistance to movement of the lead within the body tissue than does the first configuration.

2. The lead according to claim 1, wherein the modifiable portion is coaxial with the lead body.

3. The lead according to claim 1, wherein the modifiable portion is made of silicone, or polyurethane.

4. The lead according to claim 1, wherein the modifiable portion is joined to the lead body using a medical grade adhesive.

5. The lead according to claim 1, wherein the diameter of the first configuration of the modifiable portion and the lead body diameter are substantially equal.

6. The lead according to claim 1, wherein the diameter of the first configuration of the modifiable portion is less than the lead body diameter.

7. The lead according to claim 1, wherein the diameter of the second configuration of the modifiable portion is at least about 50% larger than the lead body diameter.

8. The lead according to claim 1, wherein the diameter of the second configuration of the modifiable portion is at least about 100% larger than the lead body diameter.

9. The lead according to claim 1, wherein the at least one modifiable portion has an overall length of about 4 mm to about 25 mm.

10. The lead according to claim 1, wherein the at least one modifiable portion has an overall length of about 5 mm to about 15 mm.

11. The lead according to claim 1, wherein the at least one modifiable portion has an overall length of about 8 mm to about 12 mm.

12. The lead according to claim 1, wherein the at least one modifiable portion has a width when the axial tension is released of about 2 mm to about 8 mm.

13. The lead according to claim 1, wherein the at least one modifiable portion has a width when the axial tension is released of about 3 mm to about 6 mm.

14. The lead according to claim 1, wherein the at least one modifiable portion has a width when the axial tension is released of about 3 mm to about 4 mm.

15. The lead according to claim 1, wherein the lead has at least four electrodes.

16. The lead according to claim 1, wherein there are two or more modifiable portions.

17. A kit comprising:
   an implantable medical electrical lead for electrical stimulation of body tissue comprising:
      at least one electrode;
      a lead body;
      an apparatus for applying axial tension;
      at least one modifiable portion joined to the lead body wherein the at least one modifiable portion has a first configuration and a second configuration, wherein the first configuration exists when axial tension is exerted on an exterior surface of the at least one modifiable portion by contact on the exterior surface from the apparatus, wherein the at least one modifiable portion transitions from the first configuration to the second configuration by removal of the contact by the apparatus to release the axial tension, wherein the second configuration exhibits a greater resistance to movement of the lead within the body tissue than does the first configuration, and wherein the lead body on each side of the at least one modifiable portion remains co-linear in the first configuration and the second configuration.

18. The kit according to claim 17, wherein the apparatus for applying axial tension on the at least one modifiable portion is a sheath.

19. The kit according to claim 18, wherein the sheath is made of metal or plastic.

20. A medical electrical stimulation system comprising:
   an implantable pulse generator for providing medical electrical stimulation; and
   an implantable medical electrical lead for electrical stimulation of body tissue comprising:
      at least one electrode;
      a lead body;
      at least one modifiable portion joined to the lead body wherein the at least one modifiable portion has a first configuration and a second configuration, wherein the first configuration exists when axial tension is exerted on an exterior surface of the at least one modifiable portion by contact on the exterior surface from a separate body, wherein the at least one modifiable portion transitions from the first configuration to the second configuration by removal of contact from the separate body to remove the axial tension, and wherein the second configuration exhibits a greater resistance to movement of the lead within the body tissue than does the first configuration by exhibiting a greater diameter than the first configuration.

21. A method of providing electrical stimulation of body tissue at a stimulation site employing an implantable pulse generator comprising: providing an implantable medical lead comprising:
- at least one electrode;
- a lead body;
- at least one modifiable portion joined to the lead body wherein the at least one modifiable portion has a first configuration and a second configuration, wherein the first configuration exists when axial tension is exerted on an exterior surface of the at least one modifiable portion, wherein the at least one modifiable portion transitions from the first configuration to the second configuration by removal of the axial tension, and wherein the second configuration exhibits a greater resistance to movement of the lead within the body tissue than does the first configuration; and
- at least one proximal connector element formed in a connector array in a proximal segment of the lead body;
- applying contact on the exterior surface by a separate body to apply axial tension to at least the at least one modifiable portion;
- percutaneously introducing the implantable medical lead adjacent to the stimulation site by guiding the implantable medical lead with a stylet disposed within a lumen of the implantable medical lead, the stylet being positioned within the lead body so as to extend beyond the at least one modifiable portion;
- removing contact by the separate body to remove the axial tension to at least the at least one modifiable portion such that the at least one modifiable portion transitions to the second configuration while maintaining the position of the stylet within the lumen of the lead body to thereby maintain the position of the implantable medical lead adjacent to the stimulation site;
- removing the stylet from the lumen after removing the contact by the separate body at the at least one modifiable portion; and
- coupling the at least one proximal connector element with the implantable pulse generator.

22. The method according to claim 21, wherein the separate body is an external sheath that covers at least the at least one modifiable portion.

23. The method according to claim 21 further comprising the step of using an insulated needle with both ends exposed to apply electrical stimulation through the needle using an external pulse generator in order to determine the best location for the at least one electrode.

24. The method according to claim 23 further comprising the step of testing the efficacy of the location.

25. The method according to claim 24, wherein the step of testing the efficacy of the location is accomplished by evaluating the physiologic response in relation to the electrical threshold energy required to elicit the response.

26. The method according to claim 21 further comprising
- reapplying the axial tension to at least the at least one modifiable portion;
- moving the lead; and
- removing the axial tension to at least the at least one modifiable portion.

27. The method according to claim 21, wherein the at least one modifiable portion is a segment within the lead body and wherein applying axial tension to at least the at least one modifiable portion extends the at least one modifiable portion and extends the lead body.

28. An implantable medical electrical lead for electrical stimulation of body tissue comprising:
- at least one electrode;
- a lead body; and
- at least one modifiable portion joined to the lead body wherein the at least one modifiable portion has a first configuration and a second configuration, wherein the second configuration is a bellows shape, wherein the first configuration exists when axial tension is exerted on the at least one modifiable portion by contact from a separate body, wherein the at least one modifiable portion transitions from the first configuration to the second configuration by removal of the contact by the separate body to release the axial tension, and wherein the second configuration exhibits a greater resistance to movement of the lead within the body tissue than does the first configuration.

* * * * *